United States Patent [19]

Talass

[11] Patent Number: 4,869,666

[45] Date of Patent: Sep. 26, 1989

[54] ORTHODONTIC ARCH WIRE

[75] Inventor: Mohd. F. Talass, Tokyo, Japan

[73] Assignee: Ormco Corporation, Glendora, Calif.

[21] Appl. No.: 257,750

[22] Filed: Oct. 14, 1988

[51] Int. Cl.$^4$ .............................................. A61C 7/00
[52] U.S. Cl. ................................................... 433/20
[58] Field of Search ................................... 433/20, 22

[56] References Cited

U.S. PATENT DOCUMENTS

| | | | |
|---|---|---|---|
| 4,585,414 | 4/1986 | Kottemann | 433/20 |
| 4,659,310 | 4/1987 | Kottemann | 433/20 |
| 4,717,341 | 1/1988 | Goldberg et al. | 433/9 |
| 4,731,018 | 3/1988 | Adell | 433/20 |

OTHER PUBLICATIONS

American Journal of Orthodontics, Jan. 1986, "Cosmetic Orthodontics".
"Mechanical Behavior of Optical Fibers", B. K. Tariyal et al, Bell Laboratories, pp. 161-175.
Optical Fiber Telecommunications, "Fiber Characterization Mechanical", Chapter 12, David Kalish et al, 1979, Bell Laboratories.
American Journal of Orthodontics, Mar. 1986, "Filaflex".
"Properties of Silica Glass Image Fiber", Kunio Fujiwara et al, Sumitomo Electric Industries, Ltd.
Appl. Phys. Lett., vol. 29, No. 11, Dec. 1, 1976, "Epoxy-Acrylate-Coated Fused Silica Fibers With Tensile Strengths 500 ksi (3.5 GN/m$^2$) in 1-km Gauge Lengths", H. Schonhorn et al.
Electrics Letters, vol. 14, No. 18, Aug. 31, 1978, "Furnace-Drawn Silica Fibres with Tensile Strengths 3.5 GN/m$^2$ (500 kp.s.i) in 1 km Lengths", pp. 578-579.
Hitachi Chemical Data Sheet, "Hitachi Transparent Optical Resin Molding Material", OPTOREZ OZ-1000 pp. 1-11.
International Optoelectronics Exhibition '88 Guidebook, Aoi Sansho Co., Ltd.
OPTLANE, Oki Electric Cable's Optical Transmission Lane.
Journal of Applied Physics, vol. 47, No. 10, Oct. 1976, "Tensile Strength and Fatigue of Optical Fibers", R. Olshansky et al, pp. 4497-4499.
Electronics Letters, vol. 14, No. 18, Aug. 31, 1978, "Silicone and Ethylene-Vinyl-Acetate-Coated Laser-Drawn Silica Fibres with Tensile Strengths 3.5 GN/m$^2$ (500 kp.s.i) in 3 km Lengths" pp. 603-605.
"Novel Acrylic Resin for Injection Molded Precision Lenses", Hiromasa Kawai et al, Hitachi Chemikal Co., Ltd.
Int. Journ. of Fracture, 10(1974); "Proof Testing of Ceramic Materials-an Analytical Basis for Failure Prediction", pp. 379-392, A. G. Evans et al.
Fiber and Integrated Optics, vol. 1, No. 4, "Probability of Fatigue Failure in Glass Fibers", J. E. Ritter, Jr., pp. 387-399.
Journ. of Appl. Polymer Science, vol. 23, 887-892 (1979), John Wiley & Sons, Inc., T. T. Wang et al, "Effects of Water and Moisture on Strengths of Optical Glass (Silica) Fibers Coated with a UV-Cured Epoxy Acrylate".
Applied Optics, vol. 18, No. 13, Jul. 1, 1979; "Single-mode Optical Fiber Cable", Yutaka Katsuyama et al, pp. 2232-2236.
J. Appl. Phys. 53(1), Jan., 1982, "Dynamic Fatique of Optical Fiber Under Repeated Stress", pp. 318-321.
Philips Telecommunication Review, vol. 37, No. 4, Sept. 1979, "The Manufacture of Optical Cables"; F. Krahn et al, pp. 231-240.
"Application of Fracture-Mechanics Theory to Fatigue Failure of Optical Glass Fibers", J. E. Ritter et al; J. Appl. Phys. 49(9), Sept., 1978, pp. 4779-4782.
"Silica Image Guide and Silica Light Guide for Fiberscope", Optopia, Sumitomo Electric Industries, Ltd.
"Large Core Silica Fiber for Ultra-Violet Transmission" Optopia, Sumitomo Electric Industries, Ltd.

Primary Examiner—Robert Peshock
Attorney, Agent, or Firm—Marjama & Pincelli

[57] ABSTRACT

An orthodontic arch wire for use in imparting corrective forces to teeth comprising:
an elongated central core made of a transparent or translucent material having a modulus of at least 3,000,000 pounds per square inch;
an outer layer made of a substantially transparent or translucent material which is hydrolytically stable so as to resist staining or deterioration when placed in an oral cavity.

10 Claims, 1 Drawing Sheet

ORTHODONTIC ARCH WIRE

The present invention is directed to an orthodontic arch wire for use in providing corrective forces to the teeth.

BACKGROUND OF THE INVENTION

In the practice of orthodontia, corrective forces are applied to the teeth so as to reposition them in a desired configuration. A typical orthodontic appliance system generally comprises a plurality of orthodontic brackets which are individually secured to the teeth, and an orthodontic arch wire secured to the brackets such that corrective forces are applied to the teeth. In order to transmit the appropriate force necessary to reposition the teeth, the orthodontic archwires have been typically made of metal.

Recently, in the field of orthodontia, it has been increasingly important to provide an asthetically pleasing orthodontic applicance system. As a result, orthodontic brackets made of a substantially transparent, translucent or tooth colored material have become very popular, for example, orthodontic brackets made of single or polycrystalline material, or of a ceramic material having a color substantially the same as the teeth. While these brackets have provided an improved aesthetic appearance, the arch wire is still quite visible. It has been suggested that orthodontic arch wires have an inner metal core and an outer plastic wire which can be colored so as to make it less obtrusive. An example of such orthodontic arch wires are illustrated in U.S. Pat. No. 4,659,310 and U.S. Pat. No. 4,585,414. The problem with such products is that they are opaque subject to staining, and due to the additional outer plastic layer, the size becomes greater. Another problem with such arch wires is its ability to provide the strength necessary to transmit the required corrective forces and still be relatively small in size. It has also been suggested to use fiber-reinforced composite materials for orthodontic brackets, such as illustrated in U.S. Pat. No. 4,717,341. Here again, the problem with such prior art devices is its ability to provide the appropriate strength in a relatively small size wire and the problem of staining.

Applicants have developed an orthodontic appliance system which includes an orthodontic arch wire which has an improved aesthetic appearance, and has the strength necessary to operate as an orthodontic arch-wire.

SUMMARY OF THE INVENTION

An orthodontic arch wire for use in imparting corrective forces to teeth. The arch wire comprises a central core made of substantially transparent or translucent material which has a flexural modulus of at least three million pounds per square inch. Surrounding the central core is an outer barrier layer also made of a transparent or translucent material which is hydrolytically stable so as to resist staining or deterioration when placed in an oral cavity.

DESCRIPTION OF THE PREFERRED EMBODIMENT

Figure 1:
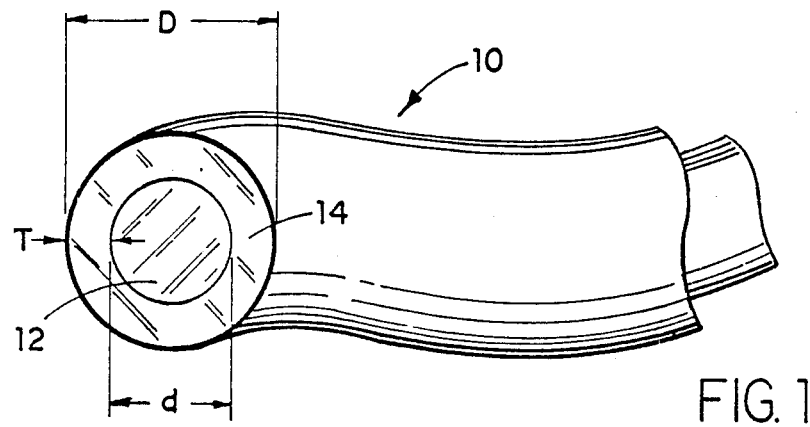
FIG. 1 is a perspective view of a portion of an orthodontic arch wire made in accordance to the present invention.

Referring to FIG. 1, there is illustrated an orthodontic arch wire 10 made in accordance with the present invention which comprises an elongated wire which is generally indicated in the figure by the number 10. The wire 10 comprises a central core 12 made of a transparent or translucent material which is less noticeable to a viewer. The core 12 is made of a material having a strength such that orthodontic forces may be transmitted thereby. The core is made of a material having a flexural modulus of at least of 3 million pounds per square inch. In the particular embodiment illustrated, the core 12 is made of quartz glass (silicone dioxide being at least 99% pure). The core 12 has a diameter d preferably no greater than about 0.01 inches. In the particular embodiment illustrated, the diameter d is approximately 0.01 inches.

Surrounding the central core 12 is an outer layer 14 made of a material which is also transparent or translucent. The outer layer 14 acts as a barrier to prevent moisture from contacting core 12 which is subject to degradation. Preferably, the outer layer 14 has a clarity substantially the same as the core 12 preferably, the difference between the refractive index of the core 12 and outer layer 14 is no greater than about 5% so that a reflective portion will not be formed at their interface. In the particular embodiment illustrated, the refractive index of the core 12 is about 1.459 and the refractive index of the outer layer 14 is about 1.410. Preferably the outer layer 14 has a refractive index slightly less than the core 12 to minimize potential reflection. The outer layer 14 is made of a material that is hydrolytically stable so as to be resistant to staining when placed in an oral environment and has a thickness T in the range from about 0.004 inches to 0.012 inches. In the particular embodiment illustrated, the outer layer 14 is made of a silicon resin and has a thickness T of about 0.004 inches.

The outer layer 14 is preferably placed about core 12 by a cladding process. This minimizes any potential degradation to core 12 and also allows bending of the wire 10 to a much smaller radius than without the layer. Wire 10 may be bent about a radius as low as 0.25 mm without any substantial damage.

In the present invention, the core 12 provides the strength necessary to transmit the corrective forces of the teeth while the outer layer 14 provides protection to the core 12 to prevent degradation which may result from placement in the oral cavity. The high strength central core helps provide a very small outer diameter D size. An arch wire made in accordance with the present invention could be made such that the outer diameter d is no greater than about 0.022 inches.

Figure 2:
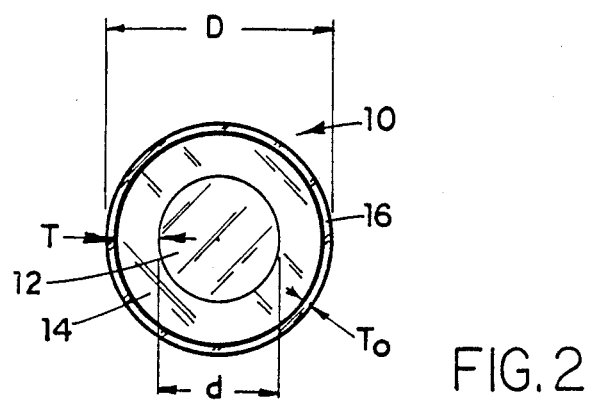
FIG. 2 is a cross-sectional view of a modified orthodontic arch wire made in accordance with the present invention.

Referring to FIG. 2, there is illustrated in cross-section, a modified arch wire 30 made in accordance with the present invention. The arch wire 30 is similar to arch wire 10, like numerals and letters indicating identical elements. In this embodiment, an optical transparent or translucent second outer layer 16 is placed around the outer layer 14 so as to impart improved abrasion resistance to the orthodontic wire as illustrated in FIG. 2. Preferably, layer 16 has a Rockwell R hardness in the range of 80 to 120. Layer 16 also preferably has a retractive index equal to or less than the refractive index of layer 14. In the embodiment illustrated, the second outer layer 16 is made out of clear plastic material such as Nylon. Outer layer 16 has a thickness To in the range of 0.002 to 0.010 inches. In the particular embodiment illustrated, To is 0.002 inches, thus wire 30 has a diameter D of about 0.022 inches. It is to be understood that layer 16 is optional and may be omitted if desired.

Figure 3:
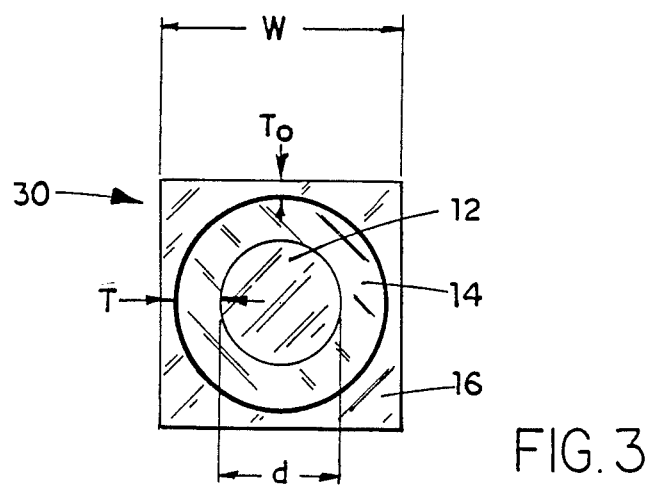
FIG. 3 is a cross-sectional view of a yet another modified orthodontic arch wire made in accordance with the present invention.

In the embodiments illustrated in FIGS. 1 and 2 the orthodontic arch wire is illustrated as having a substantially circular cross-sectioned configuration. However, the present invention is not so limited. For example, referring to FIG. 3, there is illustrated another modified form of the present invention wherein the outer layer 16 is shaped so as to have a substantially square cross-sectional configuration. This shape helps provide an orthodontic arch wire which can impart other additional corrective forces to the tooth. In this embodiment, the core 12 has a diameter d of about 0.01 inches, an outer layer 14 having a thickness T of about 0.004 inches and an outer second layer 16 having a thickness $T_o$, at its thinnest point, of about 0.002 inches thus giving an overall width W of about 0.022 inches. It is to be understood that other cross sectional shapes may be employed, for example, rectangular. In such case, the width of the short side is preferably no greater than about 0.022 inches and the width of the wide side is not greater than about 0.031 inches.

It is to be understood that various other modifications or changes can be made to the present invention without departing from the scope of the present invention. For example, but not by way of limitation, the arch wire may be straight or have a preformed configuration. The scope of the present invention being defined by the following claims.

What is claimed is:

1. An orthodontic arch wire for use in imparting corrective forces to teeth comprising:
   an elongated central core made of a transparent or translucent material having a modulus of at least 3,000,000 pounds per square inch;
   an outer layer made of a substantially transparent or translucent material which is hydrolytically stable so as to resist staining or deterioration when placed in an oral cavity.
2. An orthodontic arch wire according to claim 1 wherein the elongated central core has a refractive index substantially the same as the outer layer.
3. An orthodontic arch wire according to claim 2 wherein said elongated core has a refractive index of 1.49, and said outer layer has a refractive index of 1.410.
4. An orthodontic arch wire according to claim 1 wherein said core is made of quartz glass.
5. An orthodontic arch wire according to claim 1 wherein said core has a diameter no greater than about 0.01 inches.
6. An orthodontic arch wire according to claim 1 wherein said outer layer has a thickness in the range of 0.004 to 0.012 inches.
7. An orthodontic arch wire according to claim 1 wherein said arch wire has a substantially circular cross-sectional configuration.
8. An orthodontic arch wire according to claim 1 wherein said arch wire has substantially rectangular cross-sectional configuration.
9. An orthodontic arch wire according to claim 1 further comprising a second outer layer around said first outer layer, said second outer layer providing improved resistance to abrasion.
10. An orthodontic arch wire according to claim 1 wherein said outer layer has a refractive index less than said core.

* * * * *